(12) United States Patent
Jorgensen et al.

(10) Patent No.: US 8,309,147 B2
(45) Date of Patent: Nov. 13, 2012

(54) METHOD FOR SELECTING LIPOLYTIC ENZYME

(75) Inventors: Christel Thea Jorgensen, Copenhagen O (DK); Luise Erlandsen, Copenhagen O (DK); Kim Borch, Birkerod (DK); Jesper Vind, Vaerlose (DK)

(73) Assignee: Novozymes A/S, Bagsvaerd (DK)

( * ) Notice: Subject to any disclaimer, the term of this patent is extended or adjusted under 35 U.S.C. 154(b) by 1174 days.

(21) Appl. No.: 10/538,710

(22) PCT Filed: Dec. 11, 2003

(86) PCT No.: PCT/DK03/00850
§ 371 (c)(1),
(2), (4) Date: Jun. 10, 2005

(87) PCT Pub. No.: WO2004/053152
PCT Pub. Date: Jun. 24, 2004

(65) Prior Publication Data
US 2006/0057250 A1    Mar. 16, 2006

Related U.S. Application Data

(60) Provisional application No. 60/433,218, filed on Dec. 13, 2002.

(30) Foreign Application Priority Data

Dec. 12, 2002  (DK) ................................ 2002 01903

(51) Int. Cl.
    *A23F 3/16*    (2006.01)
(52) U.S. Cl. ......................................................... 426/52
(58) Field of Classification Search .................... 426/52
    See application file for complete search history.

(56) References Cited

U.S. PATENT DOCUMENTS

| | | | | |
|---|---|---|---|---|
| 4,478,866 A | * | 10/1984 | Ohta et al. | 426/549 |
| 4,567,046 A | * | 1/1986 | Inoue et al. | 426/20 |
| 5,183,680 A | | 2/1993 | Jodlbauer | |
| 5,354,853 A | | 10/1994 | Staveski et al. | |
| 2003/0144165 A1 | * | 7/2003 | Roggen | 510/226 |

FOREIGN PATENT DOCUMENTS

| | | | |
|---|---|---|---|
| EP | 0 869 167 A2 | | 10/1998 |
| EP | 1 108 360 | | 6/2001 |
| WO | WO 98/26057 | * | 6/1998 |
| WO | WO 00/32758 | | 6/2000 |
| WO | WO 02/03805 | | 1/2002 |
| WO | WO 02/094123 | | 11/2002 |
| WO | WO2005/040410 | | 5/2005 |

OTHER PUBLICATIONS

Burdge, G. C. 2000. A method for separation of phosphatidylcholine, triacylglycerol, non-esterfied fatty acids and cholesterol esters from plasma by solid phase extraction. British J. Nutrition. 84: 781-787.*
Helmy, F. M. et al. 1995. TLC derived data relating to the invitro deacylation of phospholipids by various extracellular phospholipase A2 compared with the in vitro deacylation of endogenous substrate by the endogenous phospholipase A2 of various tissues. J. Planar Chromatography. 8: 369-373.*
Petersen, G. et al. 2000. A rapid phospholipase D assay using zirconium precipitation of anionic substrate phospholipids:application to N-acylethanolamine formation in vitro. J. lipid Research. 41:1532-1538.*
Pomeranz, Y. et al. 1966. The lipid composition of wheat flours varying widely in bread-makin potentialities. J. Am. Oil Chem. Soc. 43:45-48.*
Ghannoum, M. A. 2000. Potential role of phohspholipids in virulence and fungal pathogenesis. Clinical Microbiol. Rev. 13:122-143.*
A.C. Eliasson et al, & k Larsson, Cereals in Breadmaking: a Molecular Collodial Approach, Ch.2, pp. 31-40 (1993).
F. Macritchie, Flour Lipids and Their Effects in Baking, J. Sci. Fd. Agric., col. 28, pp. 53-58 (1977).
F. Macritchie & P.W. Gras, The Role of Flour Lipids in Baking, Cereal Chem., vol. 50, pp. 292-302 (1973).
Marion et al, Wheat Lipids and Lipid Binding Proteins: Structure and Function (no journal or date indicated).
L.R. Trieber, Quantitative Thin-Layer Chromatography and Its Industrial Applications, ISBN 9780824775971, Published Dec. 9, 1986.
Dr David Firestone, Official Methods and Recommended Practices of the AOCS Fifth Edition First Printing pp. 1-8 (1998).
King et al, Journal of AOAC International, Comparative Evaluation of Methods Commonly Used to Determine Antimicrobial Susceptibility to Plant Extracts and Phenolic Compounds, vol. 91, No. 6, pp. 1423-1429 (2008).
Marion et al, Wheat Structure, Biochemistry and Functionality, Wheat Lipids and Lipid-Binding Proteins: Structure and Function pp. 245-260 (1995).
Marion et al, Wheat Structure, Biochemistry and Functionality Conference (1995): Reading, England pp. 1-2.
Renn et al, Ind. Engl Chem. Prod. Res. Dev, Agar and Agarose: Indispensable Partners in Biotechnology, vol. 23, pp. 17-21 (1984).
Declaration Jorn Borch Soe pp. 1-11 (Aug. 12, 2010).
Szuhaj et al , Phospholipids/Determination pp. 4519-4523 (1993).

* cited by examiner

*Primary Examiner* — D. Lawrence Tarazano
*Assistant Examiner* — Hamid R Badr
(74) *Attorney, Agent, or Firm* — Kristin J. McNamara

(57) ABSTRACT

A method of screening lipolytic enzymes is used to identify candidates for a baking additive which can improve the properties of a baked product when added to the dough. The screening method involves contacting the enzyme with N-acyl phosphatidyl ethanolamine (APE) or N-acyl lysophosphatidyl ethanolamine (ALPE), and detecting hydrolysis of an ester bond in the APE or ALPE.

2 Claims, No Drawings

METHOD FOR SELECTING LIPOLYTIC ENZYME

CROSS-REFERENCE TO RELATED APPLICATIONS

This application is a 35 U.S.C. 371 national application of PCT/DK2003/000850 filed Dec. 11, 2003, which claims priority or the benefit under 35 U.S.C. 119 of Danish application no. PA 2002 01903 filed Dec. 12, 2002 and U.S. provisional application No. 60/433,218 filed Dec. 13, 2002, the contents of which are fully incorporated herein by reference.

FIELD OF THE INVENTION

The application relates to a method of screening lipolytic enzymes to identify a candidate for use as a baking additive which can improve the properties of a baked product when added to a dough.

BACKGROUND OF THE INVENTION

It is known that various properties of a baked product can be improved by adding a lipolytic enzyme. The prior art provides a large number of lipolytic enzymes obtained from natural sources or by protein engineering. Evaluation in full-scale baking tests generally require a major effort for isolating and producing each enzyme in sufficient quantity, so screening methods are useful to select candidates for full-scale testing. WO 0032758 discloses a method of screening lipolytic enzymes for use in baking based on their activity towards ester bonds in short-chain and long-chain triglycerides, digalactosyl diglyceride and a phospholipid, particularly phosphatidyl choline (lecithin).

The lipids present in wheat flour are known to consist mainly of triglycerides, phospholipids and galactolipids. It is known that the phospholipids in wheat flour consist mainly of lyso phosphatidyl choline and phosphatidyl choline, but also include N-acyl phosphatidyl ethanolamine (APE) and N-acyl lysophosphatidyl ethanolamine (ALPE).

SUMMARY OF THE INVENTION

The inventors have developed a method of screening lipolytic enzymes to identify candidates for a baking additive which can improve the properties of a baked product when added to the dough. The improved properties may include a larger loaf volume, an improved shape factor, an improved crumb structure and/or improved dough stability e.g. improved tolerance towards extended proofing.

Accordingly, the invention provides a method of screening a lipolytic enzyme for use as a baking additive, comprising:
a) incubating the enzyme with N-acyl phosphatidyl ethanolamine (APE) or N-acyl lysophosphatidyl ethanolamine (ALPE),
b) detecting hydrolysis of an ester bond in the APE or ALPE, and
c) selecting a lipolytic enzyme which can hydrolyze an ester bond in the APE or ALPE.

The invention also provides a method of preparing a dough by adding the selected enzyme, and a method of preparing of baking the dough to prepare a baked product.

DETAILED DESCRIPTION OF THE INVENTION

Lipolytic Enzymes

The method of the invention is applicable to screening of lipolytic enzymes. The lipolytic enzymes to be tested may be chosen among the large number of lipolytic enzymes known in the prior art, e.g. those described in WO 0032758. The enzymes to be tested may include naturally occurring enzymes, particularly from microorganisms such as fungi and bacteria, as well as variants made by protein engineering, e.g. those described in WO 0032758.

The lipolytic enzymes may be tested in crude or isolated form. In particular, it may be of interest to purify the enzymes sufficiently to allow determination of the amount of enzyme protein.

APE or ALPE

The method of the invention uses a substrate which is N-acyl phosphatidyl ethanolamine (APE) or N-acyl lysophosphatidyl ethanolamine (ALPE) having the following structures, where ALPE may have the $R_1$—CO attached to the sn-1 or the sn-2 position of the lysophosphatidyl group. $R_1$—CO, $R_2$—CO and $R_3$—CO are each a fatty acyl, particularly an unsubstituted straight-chain fatty acyl group having 12-22 carbon atoms which may be saturated or unsaturated, e.g. palmitoyl (C16:0), stearoyl (C18:0), oleoyl (C18:1) or linoleoyl (C18:2).

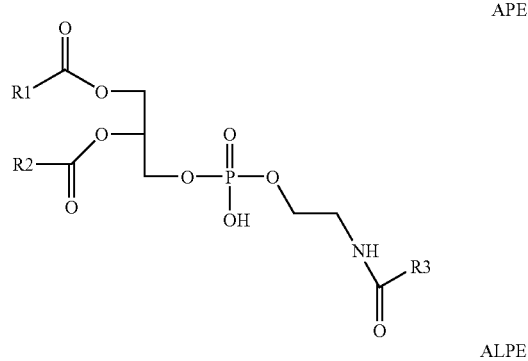

APE

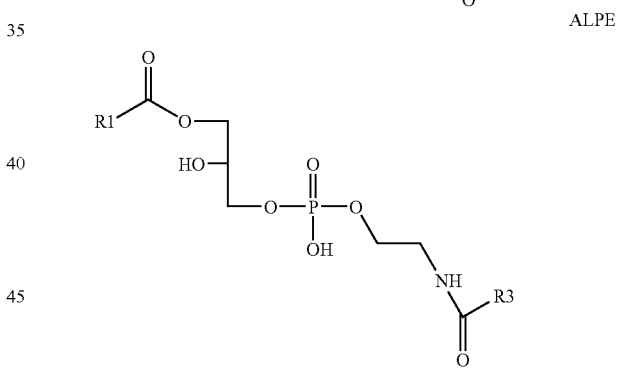

ALPE

APE and ALPE for use in the screening method may be isolated from wheat flour or may be synthesized, e.g. as described in the examples. A mixture of APE and ALPE may be used as the test substrate.

Incubation and Hydrolysis

The lipolytic enzyme activity of interest acts to hydrolyze an ester bond in APE or ALPE. Thus, when using APE as the test substrate, it liberates one or two fatty acids ($R_1$—COOH and/or $R_2$—COOH) to form ALPE or N-acyl L-alpha-glyceryl-phosphoryl-ethanolamine (N-GPE). When using ALPE as the test substrate, the activity of interest hydrolyzes ALPE into the free fatty acid $R_1$—COOH and N-acyl L-alpha-glyceryl-phosphoryl-ethanolamine (N-GPE). It may be of interest to test a number of lipolytic enzymes on the basis of equal amount of enzyme protein.

The incubation and testing of the lipolytic enzymes can conveniently be done as a plate assay, by thin-layer chromatography (TLC) or by high-performance liquid chromatography (HPLC), e.g. as described in the examples. Also, the method disclosed in Danish patent application PA 2003 01596 can be used.

Screening System

According to the invention, the lipolytic enzymes are tested for their hydrolytic activity on ester bonds in APE or ALPE. This may be combined with testing of the hydrolytic activity on ester bonds in other substrates, and the combined results may be used to select enzymes as candidates for testing in baking.

Thus, lipolytic enzymes my be selected for high activity on APE/ALPE per mg enzyme protein or for a higher activity on APE/ALPE than on PC (phosphatidyl choline, lecithin). The lipolytic enzymes may be chosen having a high hydrolytic activity on ester bonds in digalactosyl diglyceride and/or phosphatidyl choline (lecithin). The lipolytic enzyme may be chosen to have low activity on ester bonds in a $C_{16}$-$C_{20}$ triglyceride, a $C_4$-$C_8$ triglyceride, a monoglyceride, digalactosyl monoglyceride and/or lysophosphatidyl choline (lysolecithin). The tests may be carried out, e.g., as described in WO 0032758.

Use of Screening Results

Based on the hydrolytic activity towards APE/ALPE and optionally other substrates, a candidate may be selected and may be tested further by adding it to a dough and baking the dough to make a baked product. The enzyme may be added at a dosage of 0.1-10 mg enzyme protein per kg of flour, e.g. about 1 mg/kg. This may be evaluated by determining properties such as loaf volume, shape factor, crumb structure and/or dough stability e.g. tolerance towards extended proofing by conventional methods, e.g. as described in WO 0032758.

The lipolytic enzymes selected through the screening method of the invention may be added to the dough singly or in combination, e.g. as described in WO 0203805. Optionally, an additional enzyme may also be added to the dough. The additional enzyme may be another lipolytic enzyme, an amylase, particularly an anti-staling amylase, an amyloglucosidase, a cyclodextrin glucanotransferase, or the additional enzyme may be a peptidase, in particular an exopeptidase, a transglutaminase, a cellulase, a hemicellulase, in particular a pentosanase such as xylanase, a protease, a protein disulfide isomerase, e.g., a protein disulfide isomerase as disclosed in WO 95/00636, a glycosyltransferase, a branching enzyme (1,4-alpha-glucan branching enzyme), a 4-alpha-glucanotransferase (dextrin glycosyltransferase), a lactase (galacxtosidase), or an oxidoreductase, e.g., a peroxidase, a laccase, a glucose oxidase, a pyranose oxidase, a lipoxygenase, an L-amino acid oxidase or a carbohydrate oxidase.

The amylase may be a fungal or bacterial alpha-amylase, e.g. from *Bacillus*, particularly *B. licheniformis* or *B. amyloliquefaciens*, or from *Aspergillus*, particularly *A. oryzae*, a beta-amylase, e.g. from plant (e.g. soy bean) or from microbial sources (e.g. *Bacillus*). The amylase may be an antistaling amylase, as described in WO 9953769, i.e. an amylase that is effective in retarding the staling (crumb firming) of baked products, particularly a maltogenic alpha-amylase, e.g. from *Bacillus stearothermophilis* strain NCIB 11837.

Dough

The dough generally comprises wheat meal or wheat flour and/or other types of meal, flour or starch such as corn flour, corn starch, rye meal, rye flour, oat flour, oat meal, soy flour, sorghum meal, sorghum flour, potato meal, potato flour or potato starch.

The dough may be fresh, frozen or par-baked.

The dough is normally a leavened dough or a dough to be subjected to leavening. The dough may be leavened in various ways, such as by adding chemical leavening agents, e.g., sodium bicarbonate or by adding a leaven (fermenting dough), but it is preferred to leaven the dough by adding a suitable yeast culture, such as a culture of *Saccharomyces cerevisiae* (baker's yeast), e.g. a commercially available strain of *S. cerevisiae*.

The dough may also comprise other conventional dough ingredients, e.g.: proteins, such as milk powder, gluten, and soy; eggs (either whole eggs, egg yolks or egg whites); an oxidant such as ascorbic acid, potassium bromate, potassium iodate, azodicarbonamide (ADA) or ammonium persulfate; an amino acid such as L-cysteine; a sugar; a salt such as sodium chloride, calcium acetate, sodium sulfate or calcium sulfate.

The dough may comprise fat (triglyceride) such as granulated fat or shortening, but the invention is particularly applicable to a dough where less than 1% by weight of fat (triglyceride) is added, and particularly to a dough which is made without addition of fat.

The dough may further comprise an emulsifier such as mono- or diglycerides, diacetyl tartaric acid esters of mono- or diglycerides, sugar esters of fatty acids, polyglycerol esters of fatty acids, lactic acid esters of monoglycerides, acetic acid esters of monoglycerides, poly-oxyethylene stearates, or lysolecithin, but the invention is particularly applicable to a dough which is made without addition of emulsifiers (other than optionally phospholipid).

EXAMPLES

Example 1

Preparation of Substrates

Isolation of APE and ALPE from Wheat Flour

Wheat flour (1 kg) was extracted twice with MeOH (1.5 L, stirring for 30 min). The extracts were concentrated and the residue re-dissolved in hexane (1 L) and concentrated. Yield of lipid extract: 8.5 g. The lipid extract was applied to a column packed with silica gel (120 g), which was preconditioned with 1 L of hexane/2-propanol/butanol/$H_2O$ (60:30:7:3). Neutral lipids and carotenoids were removed by elution with hexane (800 mL) and then EtOAc (1.2 L). Galactolipids were removed by eluting with toluene/acetone (1:1, 800 mL, MGDG) and acetone (9 L, DGDG). Finally, phospholipids (~1.1 g) could be eluted with MeOH (1 L). The individual phospholipids could be isolated by flash chromatography ($CHCl_3$/MeOH/$H_2O$: 65:25:4) to give pure fractions of APE and ALPE. The structures were verified by $^1$H NMR and MS analysis.

N-Linoleoyl-1-oleoyl-2-hydroxy-sn-glycero-3-phosphoethanolamide (synthetic ALPE)

1-Oleoyl-2-hydroxy-sn-glycero-3-phosphoethanolamine (750 mg) was dissolved in dry chloroform (25 mL) and triethylamine (270 µL) was added under inert atmosphere. The solution was cooled on an ice bath and linoleic anhydride (930 mg, 1.1 eq.) was added dropwise with stirring. The solution was left overnight at room temperature (nitrogen atmosphere) and then concentrated to give a crude oil, which was purified by flash chromatography ($CHCl_3$/MeOH/$H_2O$) to give the pure product N-linoleoyl-1-oleoyl-2-hydroxy-sn-glycero-3-phosphoethanolamide (0.54 g, 45%). The structure was verified by $^1$H NMR ($CDCl_3$/$CD_3OD$): 5.30 ppm (m, 6H, 3×CH=CH), 3.6-3.8 ppm (m, 7H, sn-1,2,3, $CH_2OPO$), 3.12 ppm (t, 2H, $CH_2N$), 2.74 ppm (t, 2H, =CH$CH_2$CH=), 2.32 ppm (t, 2H, CH$_2$COO), 2.18 ppm (t, 2H, CH$_2$CONH), 2.00 ppm (m, 8H, CH$_2$CH=), 1.60 ppm (m, 4H, CH$_2$CH$_2$CH=), 1.30 ppm (m, $\overline{18 \times CH_2}$), 0.89 ppm (m, 6H, 2×CH$_3$).

An impure fraction (0.82 g) containing the product (~30%) and linoleic acid was collected for further purification.

Example 2

Screening by Plate Assay

Preparation of ALPE Plates

ALPE isolated from wheat flour was used to prepare plates for assay as follows:

A) 50 ml 2% agarose in purified water was melted/stirred in a microwave oven and cooled to 60° C.

B) 20 ml 2% ALPE in 0.2M NaOAc, 10 mM CaCl$_2$, pH 5.5 was kept at 60° C. for 10 min. and was blended for 30 sec. with ultrathorax.

Equal volumes of A) and B) were mixed, 100 µl 4 mg/ml crystal violet in purified water was added as indicator. The mixture was poured into appropriate petri dishes (e.g. 40 ml in a 14 cm Ø dish or 20 ml in a 9 cm Ø dish), and appropriate holes were made in the agar (3-5 mm) for application of enzyme solution.

Screening of Lipolytic Enzymes

A number of lipolytic enzymes were prepared in isolated form. The enzyme samples were diluted to a concentration corresponding to OD$_{280}$=0.5-1.0 and 10 microliter was applied into holes in the agarose/ALPE-matrix. Plates were incubated at 30° C. and clearing zones in the plates were identified after incubation for 20 hours. The results were expressed on a semi-quantitative scale from A (largest clearing zone) to E (virtually no clearing zone).

Screening Results

The *Fusarium oxysporum* lipase was chosen as a control, and a larger clearing zone than the control was observed for two of the 20 lipolytic enzymes tested.

Example 3

Screening by TLC Assay

Lipolytic Enzyme Samples

Ten lipolytic enzymes with phospholipase activity were tested for ALPE/ALPE activity and PC activity. They included two monocomponent enzymes isolated from natural sources and eight variants obtained by amino acid modification of fungal lipolytic enzymes.

TLC Assay

Each of the ten lipolytic enzymes (diluted to OD$_{280}$=0.5) was incubated with 1-2% ALPE/APE in buffer (0.1M Tris-HCl at pH 7.0 or 0.1M acetate buffer at pH 5.5) at 30-32° C. for 4 hours. After the reaction, eppendorf tubes were moved to ice-bath.

Samples for TLC were taken out and applied onto a Silica gel 60 F$_{254}$ aluminium sheet (Merck). The plate was eluted in chloroform-methanol-water 65:25:4 (v/v/v) and dried in air (fume hood). The phospholipids were visualized by dipping the plate in a bath of 10% CuSO$_4$ in 8% H$_3$PO$_4$ (fume hood) or alternatively 2 M H$_2$SO$_4$. After air-drying, the plate was heated using a heat gun (until spots visualized) or oven (5 min at 200° C.).

The exact composition of the eluent was known to strongly influence the distance of migration so freshly prepared eluents were always used. Care was taken that the TLC tank was tightly closed in order to avoid evaporation. The typical Rf values for the reference compounds were not always reproducible, so standards were always applied onto the plate:

| | |
|---|---|
| FFA (free fatty acid) | 0.80 |
| APE | 0.55 |
| ALPE | 0.40 |

Baking Performance

Each of the ten lipolytic enzymes was added to dough at a dosage in range 0.1-10 mg enzyme protein per kg flour (e.g. about 1 mg/kg).

Doughs were prepared according to a standard European straight dough procedure with 100 parts (by weight) of flour, 4 parts of yeast, 1.5 parts of salt, and 1.5 parts of sugar and water optimized to the flour. Doughs were scaled for rolls or pan bread. The volume of the bread was measured by the rape seed displacement method.

Correlation of APE/ALPE Hydrolysis and Baking

Four of the ten lipolytic enzymes were found to give good APE/ALPE hydrolysis and were also found to increase the loaf volume. The remaining six lipolytic enzymes were found to give little or no APE/ALPE hydrolysis and were also found to give little or no increase of loaf volume.

Thus, the results indicate that a lipolytic enzyme giving good APE/ALPE hydrolysis can be expected to have good baking performance.

Example 4

HPLC Test

ALPE

ALPE is dissolved in NaOAc buffer pH 5.500 micro-l substrate solution is heated for 10 min. at 30° C. 50 micro-l enzyme solution is added for a reaction period of 10-180 min. After the reaction 100 micro-l sample is inactivated at 95° C. for 5 min. 900 micro-l chloroform/methanol (1:1) is added to the sample. The total sample is centrifuged and analyzed by HPLC (Microsorb-MV 100Si 250 mm column, analytical instruments. Mobile phases: A: 80% CHCl$_3$, 19.5% MeOH, 0.5% NH$_4$OH; B: 60% CHCl$_3$, 34% MeOH, 0.5% NH$_4$OH, 5.5% H$_2$O, running with gradient. Detector: Sedere, Sedex 75 light scattering, Temp 40° C., pressure 3.5 Bar.

APE

APE and N-GPE (e.g. 1:1) are mixed in a NaOAc buffer pH 5 30° C. by mixing with an Ultra Thurax. 500 micro-l substrate solution is heated for 10 min. at 30° C. 50 micro-l enzyme solution is added for a reaction period of 10-180 min. After the reaction 100 micro-l sample is inactivated at 95° C. for 5 min. 900 micro-l chloroform/methanol (1:1) is added to the sample. The total sample is centrifuged and analyzed by HPLC (Microsorb-MV 100Si 250 mm column, analytical instruments. Mobile phases: A: 80% CHCl$_3$, 19.5% MeOH, 0.5% NH$_4$OH; B: 60% CHCl$_3$, 34% MeOH, 0.5% NH$_4$OH, 5.5% H$_2$O, running with gradient. Detector: Sedere, Sedex 75 light scattering, Temp 40° C., pressure 3.5 Bar.

Example 5

Screening by Plate Test

Preparation of Lecithin Plates pH 5.5

10 g agar in 0.1 M tri-sodium citrate dihydrate buffer (pH 5.5) in a total of 1 liter was heated in microwave oven until agar was dissolved. Then 6 g lecithin (L-a-phosphatidyl choline 95%) and 2 ml 2% crystal violet was added. The mixture was treated with an ultrathorax until lecithin was dispersed, whereafter it was poured onto lids for microtiter-plates.
Preparation of APE/ALPE Plates pH 5.5

1 g agarose was added in 50 ml $H_2O$ and heated in water bath at 65° C. until agarose was dissolved.

0.5 g APE/ALPE was added to a 0.2 M tri-sodium citrate dihydrate buffer (pH 5.5) and heated in water bath at 65° C. 0.1 ml 2% crystal violet was added and triton-x-100 was added to a concentration of 0.1%. The two solutions were mixed and the mixture was treated with an ultrathorax until APE/ALPE was dispersed, whereafter it was poured onto lids for microtiter-plates.

Plates were similarly prepared with PC (phosphatidyl choline, lecithin).
Screening of Lipolytic Enzymes

*Aspergillus* transformants expressing different lipolytic variants were inoculated in 0.2 ml YPM growth media in microtiter plates and grown for 3 days at 34° C.

96 holes were created in the lecithin plates and the APE/ALPE plates. 5 micro-l of culture supernatant was transferred to each hole and incubated at 37° C. for 20 hours. The results were expressed semi-quantitatively by to size of the clearing zone.
Correlation of APE/ALPE Hydrolysis and Baking Five variants obtained by amino acid modification of fungal lipolytic enzymes were tested by the above plate tests and also in baking tests. Four variants were found to have good baking performance (increased loaf volume), two of them showed a higher activity on APE/ALPE than on PC; one showed nearly equal activity on APE/ALPE and on PC. One showed a lower activity on APE/ALPE than on PC and was considered inconclusive as this could be caused by the enzyme amount in the culture broth being too low.

One variant was found to give poor baking performance and also showed a smaller zone on the APE/ALPE plates than on PC.

Thus, the results indicate that a lipolytic enzyme having higher activity on APE/ALPE than on PC can be expected to show good baking performance.

Example 6

Screening of Lipolytic Enzymes 14 lipolytic enzymes were tested for activity on APE/ALPE. The enzymes tested included four monocomponent enzymes isolated from natural sources and ten variants obtained by amino acid modification of fungal lipolytic enzymes. The testing was done by the method described in Danish patent application PA 2003 01596.

The 14 lipolytic enzymes were also evaluated in baking tests. Seven were found to have good baking performance (increased loaf volume), and the other seven were found to give poor baking performance.

A comparison of baking performance and APE/ALPE activity showed that the seven enzymes with good baking performance gave had a higher APE/ALPE activity than the seven with poor baking performance.

Thus, the results indicate that a lipolytic enzyme having a relatively high activity on APE/ALPE (per mg enzyme protein) can be expected to show good baking performance.

The invention claimed is:

1. A method of selecting a lipolytic enzyme for use as a baking additive, comprising:
   a) incubating at least one lipolytic enzyme with N-acyl phosphatidyl ethanolamine (APE) or N-acyl lysophosphatidyl ethanolamine (ALPE),
   b) detecting hydrolysis of an ester bond in the APE or ALPE,
   c) incubating the at least one lipolytic enzyme with phosphatidyl choline (PC),
   d) detecting hydrolysis of an ester bond in the PC, and
   e) selecting a lipolytic enzyme which has a higher hydrolytic activity on the ester bond in the APE or ALPE than on the ester bond in the PC.

2. The method of claim 1 wherein the incubation and detection comprise a plate assay, thin-layer chromatography (TLC) or high-performance liquid chromatography (HPLC).

* * * * *